(12) United States Patent
Liu et al.

(10) Patent No.: US 9,360,415 B2
(45) Date of Patent: *Jun. 7, 2016

(54) DYNAMIC RECONSTRUCTION OF A CALIBRATION STATE OF AN ABSORPTION SPECTROMETER

(71) Applicant: SpectraSensors, Inc., Rancho Cucamonga, CA (US)

(72) Inventors: Xiang Liu, Rancho Cucamonga, CA (US); John Lewison, Corona, CA (US); Wenhai Ji, Fontana, CA (US); Alfred Feitisch, Rancho Cucamonga, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,942

(22) Filed: Apr. 28, 2014

(65) Prior Publication Data

US 2014/0253922 A1    Sep. 11, 2014

Related U.S. Application Data

(63) Continuation-in-part of application No. 13/235,105, filed on Sep. 16, 2011, now Pat. No. 8,711,357.

(60) Provisional application No. 61/405,589, filed on Oct. 21, 2010.

(51) Int. Cl.
*G01N 21/00* (2006.01)
*G01N 21/27* (2006.01)
(Continued)

(52) U.S. Cl.
CPC ........... *G01N 21/274* (2013.01); *G01J 3/28* (2013.01); *G01J 3/42* (2013.01); *G01N 21/031* (2013.01);
(Continued)

(58) Field of Classification Search
CPC .............................. G01N 21/39; G01N 21/274

USPC ........................................................ 356/437
See application file for complete search history.

(56) References Cited

U.S. PATENT DOCUMENTS

| | | | |
|---|---|---|---|
| 3,995,960 A | 12/1976 | Fletcher et al. | |
| 5,026,991 A | 6/1991 | Goldstein et al. | |

(Continued)

FOREIGN PATENT DOCUMENTS

| | | | |
|---|---|---|---|
| DE | 3619301 A1 | 12/1987 | |
| EP | 1111369 A1 | 6/2001 | |
| WO | WO-2012054886 A1 | 4/2012 | |

OTHER PUBLICATIONS

Weldon et al. "$H_2S$ and $CO_2$ gas sensing using DFB laser diodes emitting at 1.57 μm". Sensors and Actuators B, vol. 29. pp. 101-107 (1995).

*Primary Examiner* — Tarifur Chowdhury
*Assistant Examiner* — Omar Nixon
(74) *Attorney, Agent, or Firm* — Mintz Levin Cohn Ferris Glovsky and Popeo, P.C.

(57) ABSTRACT

A reference harmonic absorption curve of a laser absorption spectrometer can have a reference curve shape derived from a reference signal generated by the detector in response to light passing from the laser light source through a reference gas or gas mixture. The reference gas or gas mixture can include one or more of a target analyte and a background gas expected to be present during analysis of the target analyte. A test harmonic absorption curve having a test curve shape is compared with the reference harmonic absorption curve to detect a difference between the test curve shape and the reference curve shape. Operating and/or analytical parameters of the laser absorption spectrometer are adjusted to correct the test curve shape to reduce the difference between the test curve shape and the reference curve shape.

25 Claims, 3 Drawing Sheets

(51) Int. Cl.
*G01N 21/39* (2006.01)
*G01N 21/3504* (2014.01)
*G01J 3/28* (2006.01)
*G01J 3/42* (2006.01)
*G01N 21/03* (2006.01)
*G01N 21/31* (2006.01)
*G01N 21/3518* (2014.01)

(52) U.S. Cl.
CPC ............ *G01N 21/31* (2013.01); *G01N 21/3504* (2013.01); *G01N 21/3518* (2013.01); *G01N 21/39* (2013.01); *G01N 2021/399* (2013.01)

(56) References Cited

U.S. PATENT DOCUMENTS

| | | | |
|---|---|---|---|
| 5,267,019 A | 11/1993 | Whittaker et al. | |
| 5,427,955 A * | 6/1995 | Shattuck | G01N 21/63 356/433 |
| 5,536,172 A * | 7/1996 | Shattuck | G01N 21/63 436/124 |
| 6,064,488 A | 5/2000 | Brand et al. | |
| 6,795,190 B1 * | 9/2004 | Paul et al. | 356/437 |
| 7,704,301 B2 | 4/2010 | Zhou et al. | |
| 7,819,946 B2 | 10/2010 | Zhou et al. | |
| 8,152,900 B2 | 4/2012 | Zhou et al. | |
| 8,500,849 B2 | 8/2013 | Zhou et al. | |
| 8,711,357 B2 | 4/2014 | Liu et al. | |
| 2003/0134427 A1 | 7/2003 | Roller et al. | |
| 2003/0189709 A1 | 10/2003 | Maynard et al. | |
| 2004/0034480 A1 | 2/2004 | Binder | |
| 2006/0011844 A1 | 1/2006 | Oka et al. | |
| 2007/0195318 A1 | 8/2007 | Yamamoto | |
| 2007/0246653 A1 * | 10/2007 | Zhou | 250/339.1 |

* cited by examiner

DYNAMIC RECONSTRUCTION OF A CALIBRATION STATE OF AN ABSORPTION SPECTROMETER

RELATED SUBJECT MATTER

This is a continuation-in-part of U.S. application Ser. No. 13/235,105 filed Sep. 16, 2011 and issued on Apr. 29, 2014 as U.S. Pat. No. 8,711,357 entitled "Dynamic Reconstruction of a Calibration State of an Absorption Spectrometer," which claims priority under 35 U.S.C. §119(e) to U.S. provisional application No. 61/405,589 filed on Oct. 21, 2010 and entitled "Dynamic Reconstruction of a Calibration State of an Absorption Spectrometer." The current application is also related to co-owned U.S. Pat. No. 7,819,946 entitled "Reactive Gas Detection in Complex Backgrounds," co-pending and co-owned U.S. patent application Ser. No. 13/026,921 filed on Feb. 14, 2011 and issued on Jan. 22, 2013 as U.S. Pat. No. 8,357,417 entitled "Spectrometer with Validation Cell," and co-pending and co-owned U.S. patent application Ser. No. 13/027,000 filed on Feb. 14, 2011 and issued on Feb. 2, 2015 as U.S. Pat. No. 8,953,165 entitled "Validation and Correction of Spectrometer Performance Using a Validation Cell." The entirety of the disclosure of each application or patent listed in this paragraph is incorporated by reference herein.

TECHNICAL FIELD

The subject matter described herein generally relates to laser spectroscopy and the calibration of absorption spectrometers.

BACKGROUND

Frequency stabilization of a tunable laser light source can be critical for quantitative trace gas absorption spectroscopy. Depending on the operational wavelength, a tunable laser source such as a diode lasers can typically exhibit a wavelength drift on the order of a few picometers (on the order of gigahertz) per day to fractions of picometers per day. A typical trace gas absorption linewidth can in some instances be on the order of a fraction of a nanometer to microns. Thus, drift of the laser light source can, over time, introduce critical errors in identification and quantification of trace gas analytes, particularly in gas having one or more background compounds whose absorption spectra might interfere with absorption features of a target analyte.

SUMMARY

In one aspect of the currently described subject matter, a method includes retrieving, for example from a computer-readable storage medium or device, at least one reference harmonic absorption curve of a laser absorption spectrometer that includes a tunable laser light source and a detector. Each reference harmonic absorption curve has a reference curve shape and includes a first, second, or higher order harmonic signal of a reference signal generated by the detector in response to light passing from the laser light source through a reference gas or gas mixture. The reference gas or gas mixture includes one or more of a target analyte and a background gas expected to be present during analysis of the target analyte. The reference harmonic absorption curve is determined for the laser absorption spectrometer in a known or calibrated state, reflecting the laser scanning behavior in the spectroscopic wavelength space and the resulting, calibrated, quantification of the absorption signal. A test harmonic absorption curve having a test curve shape is compared with the at least one reference harmonic absorption curve to detect a difference between the test curve shape and the reference curve shape that exceeds a predefined allowed deviation and therefore indicates a change in an output of the laser light source and the detection circuit relative to the calibrated state. One or more operating and analytical parameters of the laser absorption spectrometer and the detector circuit are adjusted to correct the test curve shape to reduce the difference between the test curve shape and the reference curve shape.

In interrelated aspects of the current subject matter, an apparatus can include a tangibly embodied machine-readable medium operable to or otherwise storing instructions that cause one or more machines (e.g., computers, programmable processors, etc.) to perform operations as described herein. Similarly, computer systems are also described that may include at least one processor and a memory coupled to the at least one processor. The memory may include one or more programs that cause the at least one processor to perform one or more of the operations described herein. A spectrometer can include a machine readable medium, at least one processor, a light source, and a detector.

In optional variations, one or more additional features, including but not necessarily limited to those described in this and the following paragraphs of this section of the application, can also be included. A field validation metric of the laser absorption spectrometer that includes at least one of the difference between the test curve shape and the reference curve shape, an identification of the one or more operating and analytical parameters that were adjusted, and a value by which the one or more operating and analytical parameters were adjusted can be promoted. The promoting can include, but is not limited to, one or more of displaying on a display device of a computing system or portable device, sending an electronic alert message over a network to a device or user, generating a alert (i.e. visual, auditory, tactile, etc.), generating a telephonic or facsimile transmission, storing an alert message and/or associated data to a computer-readable storage medium, and the like.

The one or more operating and analytical parameters of the laser absorption spectrometer can include at least one of laser light source parameters, detector parameters, and signal conversion parameters used in generating the test harmonic absorption curve from a signal produced by the detector. The laser light source parameters can include at least one of a temperature, an operating current, a modulation current, a modulation current frequency, a modulation current amplitude profile, a modulation current frequency profile, a ramp current, a ramp current frequency, a ramp current frequency profile, a ramp current amplitude profile, an optical beam profile and an optical power. The detection circuit parameters can include at least one of a gain and a phase setting and measurement timing of the detection circuit with respect to the laser frequency modulation. The signal conversion parameters can include at least one of a gain and a phase setting and a timing setting of the demodulating device.

The output can include a light intensity as a function of wavelength over a wavelength scan range. The laser light source can include at least one of a tunable diode laser, a tunable semiconductor laser, a quantum cascade laser, an intra-band cascade laser (ICL) a vertical cavity surface emitting laser (VCSEL), a horizontal cavity surface emitting laser (HCSEL), a distributed feedback laser, a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, a thermal emitter, a device capable of generating frequency tunable light through non-linear optical interactions (e.g. via a Raman method, optical parametric oscillation, etc.), and the like. The detector can include for example, one or more of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, a photo-multiplier, and the like. The laser absorption spectrometer can further include a signal detection circuit that allows adjustment of a signal phase of the laser light source with respect to a modulation current phase. The laser absorption spectrometer can further include a signal detection circuit that allows adjustment of frequency filters. The laser absorption spectrometer can further include a signal detection circuit that allows adjustment of DC and AC gain. The laser absorption spectrometer may further include a laser frequency stabilization circuit based upon a suitable molecular absorption line. The laser absorption spectrometer can optionally further include a laser frequency stabilization circuit based upon a suitable optical system generating optical wavelength transmission markers with well defined wavelength spacing.

The comparing can further include applying a curve fitting algorithm to quantify the difference between the test curve shape and the reference curve shape. The comparing can further include applying at least one of subtracting, dividing, cross correlation, curve fitting, and multivariable regression for one or more parts or the entire of the test curve and the reference curve, and computing one or more of the difference, the ratio, the mean square error (MSE), the coefficient of determination (R2), the cross correlation function/integral and the regression coefficients in the light intensity (i.e., the y-axis) and/or the wavelength (i.e. the x-axis) domain to quantify the difference between the test curve shape and the reference curve shape.

The reference curve can include at least one of a calibration reference curve stored during calibration of the laser absorption spectrometer and a curve constructed using one or more stored calibration reference curves selected according to a composition of the background gas and/or the concentration of the target analyte. The method can further include obtaining the test harmonic absorption curve, which can include passing light comprising a scanned wavelength range and an imposed modulation frequency from the light source through a volume of gas, and converting a signal from the detector to the test harmonic curve. The converting can include demodulating the signal at the first, the second, or the higher order harmonic frequency of the imposed modulation frequency. The converting can make use of more than one harmonic order of the signal.

The volume of gas can include one of a sample cell filled with a test gas comprising a known or unknown concentration of the target analyte, the sample cell filled with the background gas, a reference gas volume disposed in a path of the light and containing the test gas with the known or unknown concentration of the target analyte, and the reference gas volume disposed in the path of the light and containing only the background gas or gas mixture. The sample cell can include a simple pass through with the laser beam reaching the optical detector without optical reflection of the laser beam. The sample cell can include a multiple-pass configuration in which the light is reflected between one or more optically reflective mirrors while the light remains inside the sample cell. The sample cell can include a multiple pass configuration routing the beam by refractive optical means. The sample cell can include at least one of a Herriot Cell, an off axis optical resonator cell and a super high finesse optical cavity.

The method can further include checking fidelity of the laser absorption spectrometer by one or more of analyzing a premixed calibration sample from a premixed container, a prepared calibration sample generated using a permeation device, a non absorbing zero gas, and a non absorbing zero gas contained in a reference volume.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

To address the above-noted and potentially other issues with currently available solutions, one or more implementations of the current subject matter provide methods, systems, articles of manufacture, and the like that can, among other possible advantages, provide an automated, algorithmic approach that frequency stabilizes a tunable laser light source of a laser absorption spectrometer to improve the robustness of quantitative trace gas concentration measurements by compensating and/or correcting for short term ambient changes in analytical conditions as well as long term drift and aging effects that may adversely affect performance of the laser absorption spectrometer.

Real time laser frequency stabilization can be achieved in some implementations by comparing actual absorption spectra collected at the time of calibration of an instrument with absorption spectra collected in the field for gas samples without need for a molecular reference cell and a separate laser frequency stabilization circuit. Aside from increased cost and complexity, a separate laser frequency stabilization circuit can also interfere with the actual measurement. The current subject matter can reduce cost and complexity while also improving operating robustness and measurement fidelity and reproducibility compared to previously available spectroscopy approaches based on frequency stabilization onto a molecular line which is not part of the actual measurement. Using an approach as described herein, information about the performance of a laser spectrometer relative to a previous known or calibrated state can be obtained across the breadth of a scanned wavelength range of a tunable or scannable laser light source. Such an approach can provide substantial improvement relative to techniques that focus only on peak location rather than an entire absorption curve shape over a broader range of wavelengths.

Figure 1:
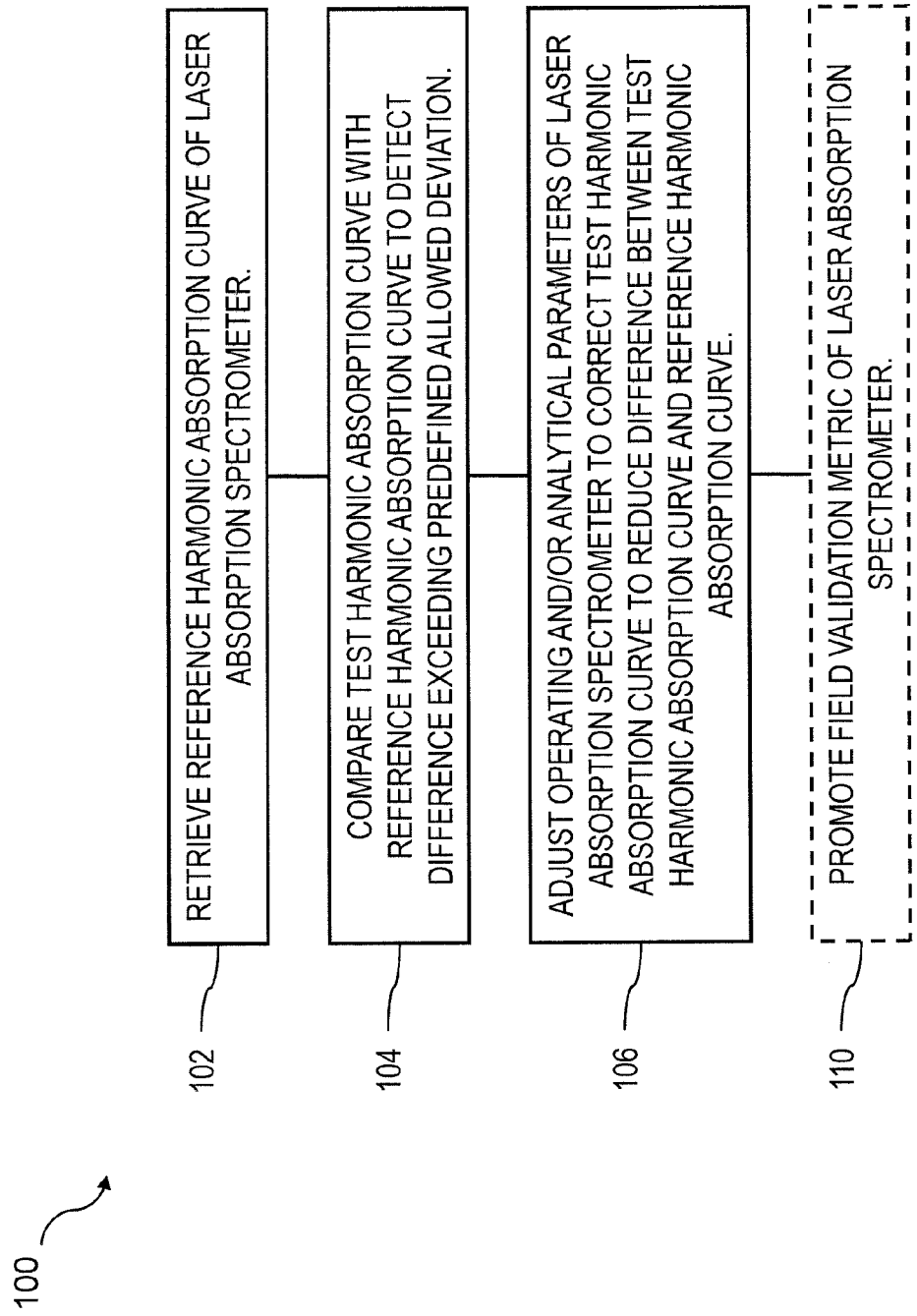
FIG. 1 illustrates a process flow diagram illustrating aspects of a method consistent with implementations of the current subject matter.

FIG. 1 shows a process flow chart 100 illustrating features consistent with an implementation of the current subject matter. At 102, one or more reference harmonic absorption curves that can be obtained through analysis of one or more reference gas mixtures by a laser absorption spectrometer is/are retrieved, for example from local or networked data storage. The one or more reference harmonic absorption curves that can have been previously obtained through analysis of one or more reference gas mixtures by a laser absorption spectrometer, for example at factory calibration or at another time when the laser absorption spectrometer is in a well-calibrated state, and stored for later retrieval. At 104, a test harmonic absorption curve is compared with the at least one of the one or more reference harmonic absorption curves to detect a difference between the respective curve shapes that exceeds a predefined allowed deviation. At 106, the operating and/or analytical parameters of the laser absorption spectrometer are adjusted to correct the test harmonic absorption curve to reduce the detected difference between the test harmonic absorption curve shape and the reference harmonic absorption curve shape. In other words, after adjusting of the one or more operating and/or analytical parameters of the laser absorption spectrometer, a subsequent test harmonic absorption curve more closely resembles the reference harmonic absorption curve. Optionally, at 110, a field validation metric of the laser absorption spectrometer can be promoted. The field validation metric can include at least one of the difference between the test curve shape and the reference curve shape, an identification of the one or more operating and analytical parameters that were adjusted, and a value by which the one or more operating and analytical parameters were adjusted.

The adjusting of the one or more operating and/or analytical parameters of the laser absorption spectrometer to reduce the detected difference between the test harmonic absorption curve shape and the reference harmonic absorption curve shape can be performed by a variety of approaches. In one implementation, an iterative approach can be used. In one non-limiting implementation, one of several potential operating and/or analytical parameters of the laser absorption spectrometer can be adjusted and a new test harmonic absorption curve generated by the laser absorption spectrometer. Adjustments to the selected parameter can continue with successive generation of new test harmonic absorption curves until a setting of maximum improvement in the difference between a test harmonic absorption curve and the reference harmonic absorption curve is obtained. Then another parameter can be iteratively adjusted in a similar manner until each parameter has been so adjusted. Any algorithm usable for iteratively converging to a multi-variate solution can be used.

The test curve can be collected using a reference gas with known concentration of a target analyte, or with a sample gas having a known or unknown concentration of the analyte or even not containing the analyte (i.e., only the background gas or mixture). If the test curve is collected with a unknown concentration of the target analyte, a reference curve can be constructed using one or more stored reference curves according to a previously measured target analyte concentration (i.e. the target analyte concentration obtained for a measurement immediately or otherwise proceeding the current measurement) and then compare the test curve with the constructed reference curve. Alternatively, only part of the test curve that is not affected by the concentration of the analyte can be compared. For example, the part of the curve that arises only due to absorption of the background gases.

The exact shape of the test curve, and the concentration calculation of the one or more target analytes for which the laser absorption spectrometer is configured to analyze can depend critically upon the laser frequency behavior. The laser frequency behavior can be affected by one or more operating and environmental parameters that can include, but are not limited to the center frequency, the ramp current, the modulation current, and other parameters of the laser light source as well as one or more parameters of the sample cell, detector, demodulator, and the like. The center frequency of the laser light source can be affected by at least the operating temperature and the operating current of the laser light source. The particular frequency changes caused by changes in drive and/or modulation current, temperature, and the like can be quite specific to each individual laser light source.

A curve correlation algorithm according to implementations of the current subject matter can generate an error signal whenever the laser frequency changes, (i.e. if the same reference gas that was used to record the original reference trace is periodically analyzed). The reference harmonic absorption curve can be stored once, when the analyzer receives its original calibration in the factory. Alternatively or in addition, the reference harmonic absorption curve can be updated periodically using a differential spectroscopy approach, for example as described in co-owned U.S. Pat. No. 7,819,946 to adjust for stream changes, while maintaining a basic reference from the original calibration.

Figure 2:
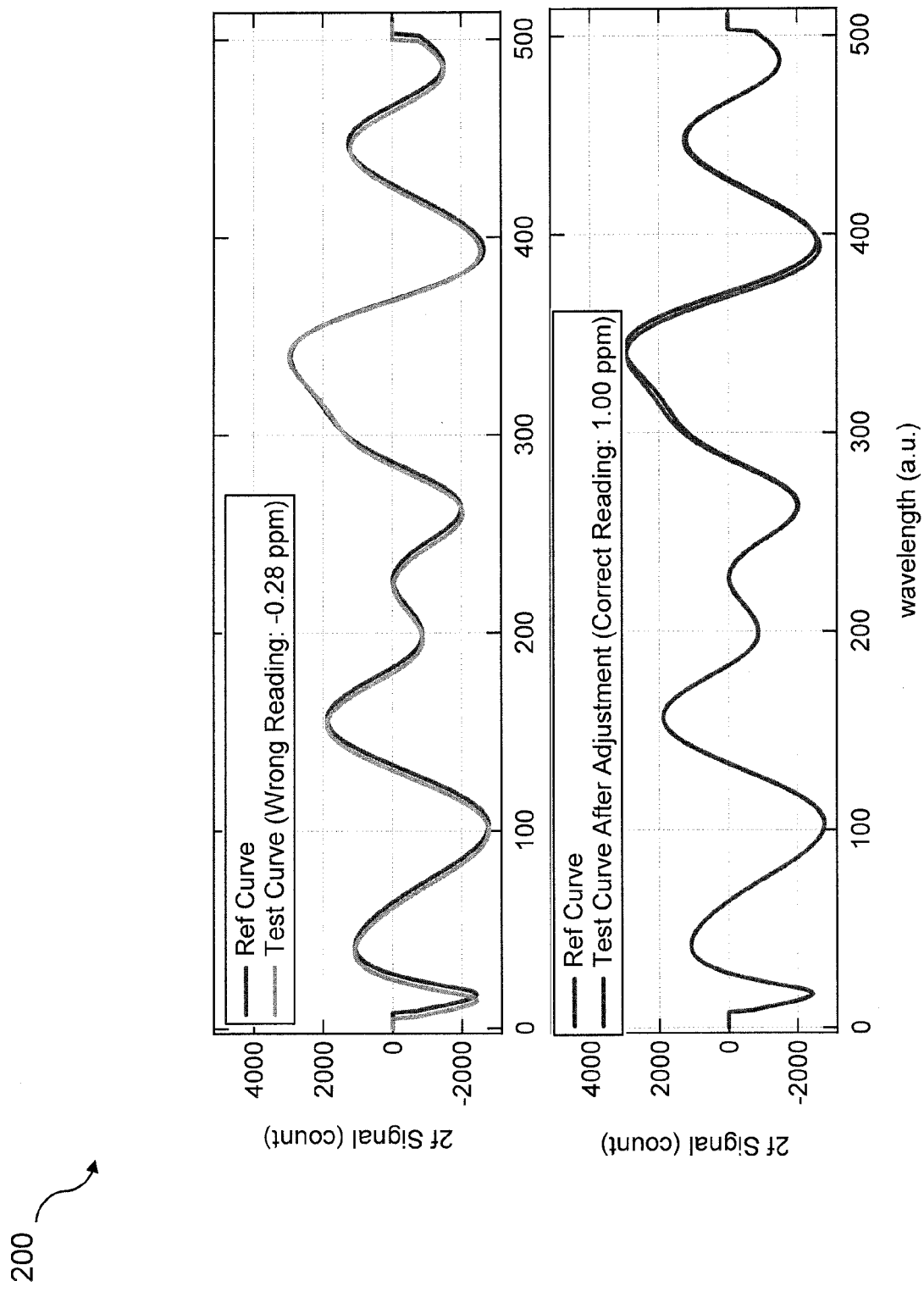
FIG. 2 illustrates two spectral absorption charts showing an example of adjusting a middle operating current of a laser light source to shift a test curve to align with a stored reference curve.
Figure 3:
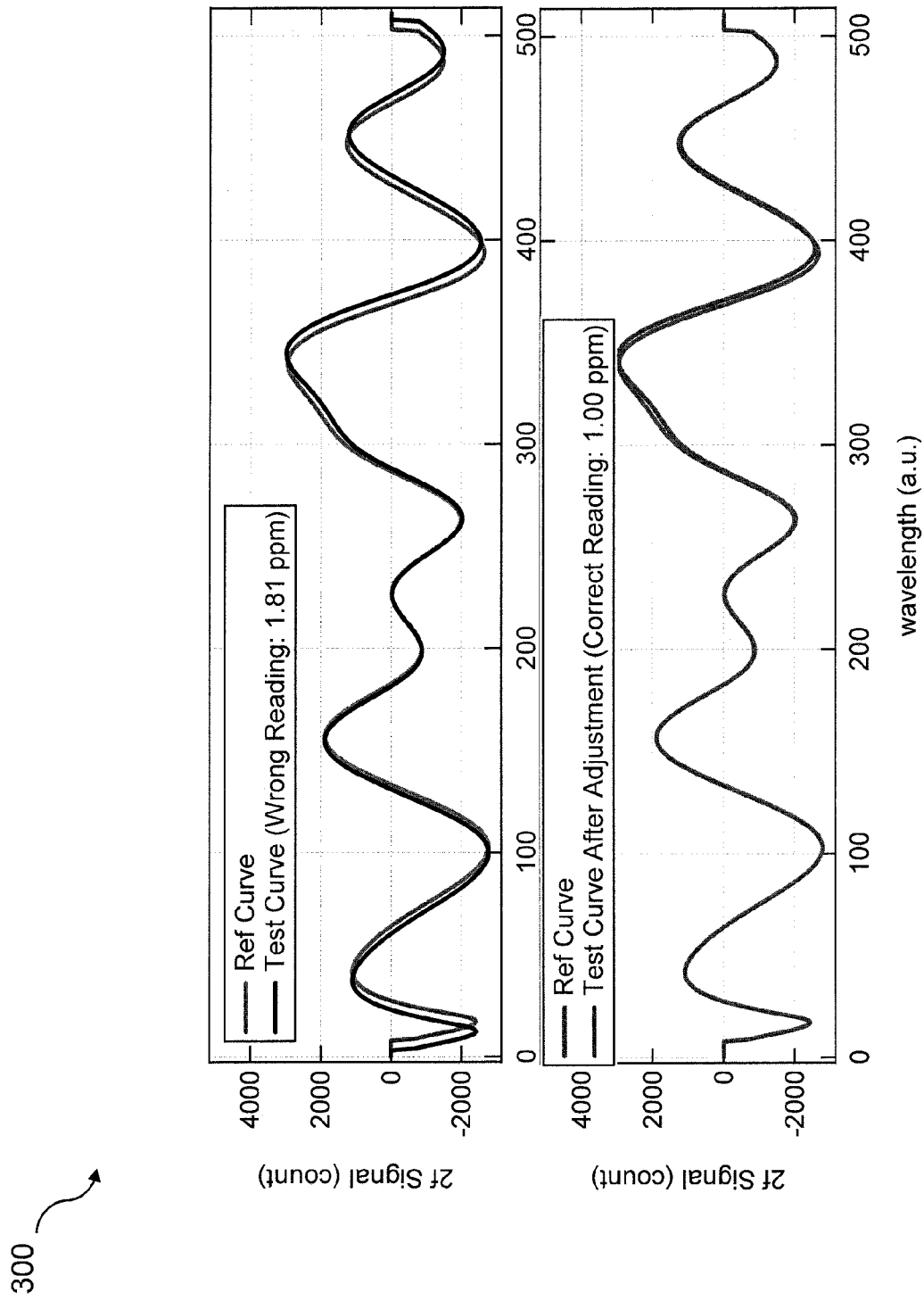
FIG. 3 is two spectral absorption charts showing an example of adjusting one or more operating parameters of a laser light source and/or signal converting parameters to correct a test curve shape to reduce the difference between the test curve shape and a reference curve shape.

Upon receiving an error signal, an optimization algorithm can engage to adjust or otherwise reset one or more operating and analytical parameters of the laser absorption spectrometer, which can include but are not limited to laser temperature, operating current, modulation current, ramp current, and other signal detection and conversion parameters, to automatically reconstruct the exact harmonic absorption curve shape as was originally stored during factory calibration FIG. 2 and FIG. 3 show two examples of dynamic corrections to a calibration state of a spectrometer using sample data. The reference curve shown in the top and bottom panels of FIG. 2 is obtained with a tunable diode laser spectrometer for a reference gas mixture containing approximately 25% ethane and 75% ethylene. The test curve shown on the top panel of FIG. 2 is obtained using the same spectrometer after some time had passed for a test gas mixture containing 1 ppm acetylene in a background of approximately 25% ethane and 75% ethylene. Acetylene has a spectral absorption feature in the range of about 300 to 400 on the wavelength axis of the charts in FIG. 2. In an example in which drift and/or other factors affect the spectrometer performance over time, the test curve can be shifted (for example to the left as shown in FIG. 2) compared with the reference curve. Absent a correction to the test curve, the measured concentration of acetylene from the spectrometer would be −0.29 ppm instead of the correct value of 1 ppm.

According to an approach consistent with implementations of the current subject matter, the amount of the test curve drift can be identified by comparing the test and reference curves in a portion of the spectrum outside of the area where the acetylene absorption feature occurs (i.e. the region between about 20-260 on the wavelength axis). The laser middle operating current can be adjusted to shift the test curve back to align up with the reference curve as shown in the bottom panel of FIG. 2. After the adjustment, the measured concentration of acetylene from the spectrometer is 1 ppm.

The reference curve in the top and bottom panels of FIG. 3 is also obtained with a tunable diode laser spectrometer for a reference gas mixture containing approximately 25% ethane and 75% ethylene. The test curve on the top panel of FIG. 3 was obtained for a test gas mixture containing 1 ppm acetylene in a background of approximately 25% ethane and 75% ethylene. As shown in the top panel of FIG. 3, the test curve shape is distorted relative to the shape of the reference curve due to drift or other factors affecting performance of the laser absorption spectrometer over time. If the test curve is not corrected, the measured concentration of acetylene in the test gas mixture determined by the spectrometer can be, for example, 1.81 ppm instead of the true concentration of 1 ppm.

According to an approach consistent with implementations of the current subject matter, the amount of test curve distortion can be identified and/or corrected for by comparing one or more sections of the test curve and reference curve in one or more portions of the spectrum outside of the area where the acetylene absorption feature occurs (i.e. the regions between about 20-260 and 400-500 on the wavelength axis). The laser operating parameters and signal converting parameters can be adjusted to correct the test curve shape to more closely resemble the reference curve shape. After the adjustment, the measured concentration of acetylene from the spectrometer turns to 1 ppm.

The approaches illustrated in FIG. 2 and FIG. 3 use a reference harmonic spectrum collected for a sample having a background composition consistent with that expected to be present under analytical conditions during which the target analyte (acetylene) is to be quantified. In an alternative or additional implementation, the reference harmonic spectra can be selected to contain one or more background absorption peaks that do not change with background compositions. In an alternative or additional implementation, the reference harmonic spectrum can be constructed from reference absorption spectra of individual background species.

As described and illustrated, implementations of the current subject matter can consider substantially more information regarding the exact shape of a reference harmonic absorption curve than is typically used in peak locking. Previously available laser control loops are generally limited to only stabilizing or tracking the laser frequency and/or peak position (i.e. location of the peak of a spectral feature in the digitized scan range of the measurement).

The approach described herein can be applicable to any laser absorption spectrometer that includes a tunable laser source, including but not limited to direct absorption spectrometers, harmonic absorption spectrometers, differential absorption spectrometers, etc. For a direct absorption spectrometer, the measurement of target analyte concentrations can be performed without using a harmonic conversion or demodulation of the signal obtained from the detector. However, periodic or continuous recalibration of the laser light source, detector, etc. can be performed using a calibration circuit, etc. that makes use of a harmonic signal obtained from the detector signal.

In another implementation, the calibration state of a harmonic absorption spectrometer can be validated using different operating parameters, including but not limited to the modulation frequency, ramp frequency, etc., than are used in identifying and/or quantifying a target analyte. Use of larger modulation frequencies can increase the signal to noise ratio of an absorption feature of a target analyte by relatively reducing the impact of absorption by the background composition of a gas mixture. However, as the current subject matter can make use of information obtained from all absorption features that occur across a laser scan range in verifying agreement between a test harmonic absorption curve and a reference harmonic absorption curve, it can be advantageous to collect both the test and reference harmonic absorption curves under conditions that lead to a more complicated spectrum so that additional features are available to be matched between the test and reference harmonic absorption curves.

Aspects of the subject matter described herein can be embodied in systems, apparatus, methods, and/or articles depending on the desired configuration. In particular, various implementations of the subject matter described herein can be realized in analog or digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be implemented in a computing system that includes a back-end component, such as for example one or more data servers, or that includes a middleware component, such as for example one or more application servers, or that includes a front-end component, such as for example one or more client computers having a graphical user interface or a Web browser through which a user can interact with an implementation of the subject matter described herein, or any combination of such back-end, middleware, or front-end components. A client and server are generally, but not exclusively, remote from each other and typically interact through a communication network, although the components of the system can be interconnected by any form or medium of digital data communication. Examples of communication networks include, but are not limited to, a local area network ("LAN"), a wide area network ("WAN"), and the Internet. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed:

1. A method for implementation by one or more data processors comprising:

retrieving, by at least one data processor, a reference harmonic absorption curve of a laser absorption spectrometer, the laser absorption spectrometer comprising a tunable or scannable laser light source and a detector, the reference harmonic absorption curve having a reference curve shape and comprising a first, second, or higher order harmonic signal of a reference signal generated by the detector in response to light passing from the laser light source through a reference gas or gas mixture, the reference gas or gas mixture comprising one or more of a target analyte and a background gas expected to be present during analysis of the target analyte, the reference harmonic absorption curve having been determined for the laser absorption spectrometer in a known or calibrated state;

comparing, by at least one data processor, at least one portion of a test harmonic absorption curve having a test curve shape with at least one portion of the reference harmonic absorption curve to detect a difference between the test curve shape and the reference curve shape that exceeds a predefined allowed deviation and therefore indicates a change in an output of the laser light source relative to the known or calibrated state, wherein one or more portions of the test harmonic absorption curve is compared with one or more portions of the reference harmonic absorption curve arising due to absorption of the background gases and not by absorption of the target analyte; and causing, by at least one data processor, one or more operating and analytical parameters of the laser absorption spectrometer to be adjusted based on the comparing.

2. A method as in claim 1, further comprising promoting, by at least one data processor, a field validation metric of the laser absorption spectrometer, the field validation metric comprising at least one of the difference between the test curve shape and the reference curve shape, an identification of the one or more operating and analytical parameters that were adjusted, and a value by which the one or more operating and analytical parameters were adjusted.

3. A method as in claim 1, wherein the one or more operating and analytical parameters of the laser absorption spectrometer comprise at least one of laser light source parameters, detector parameters, and signal conversion parameters used in generating the test harmonic absorption curve from a signal produced by the detector.

4. A method as in claim 3, wherein the laser light source parameters comprise at least one of a temperature, an operating current, a modulation current, a ramp current, and a phase of the laser light source; the detector parameters comprise at least one of a gain and a phase setting of a detector circuit; and the signal conversion parameters comprise at least one of a gain and a phase setting of a demodulating device.

5. A method as in claim 1, wherein the output comprises a light intensity as a function of wavelength over a wavelength scan range.

6. A method as in claim 1, wherein
the light source comprises at least one of a tunable diode laser, a tunable semiconductor laser, a quantum cascade laser, an intra-band cascade laser (ICL) a vertical cavity surface emitting laser (VCSEL), a horizontal cavity surface emitting laser (HCSEL), a distributed feedback laser, a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, a thermal emitter, and a device capable of generating frequency tunable light through nonlinear optical interactions; and
the detector comprises at least one of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, and a photo-multiplier.

7. A method as in claim 1, wherein the comparing further comprises applying a curve fitting algorithm to quantify the difference between the test curve shape and the reference curve shape.

8. A method as in claim 1, wherein the comparing further comprises applying at least one of subtracting, dividing, cross correlation, curve fitting, and multivariable regression for one or more parts or the entirety of the test curve and the reference curve, and computing one or more of the difference, the ratio, the mean square error (MSE), the coefficient of determination ($R^2$), the cross correlation function/integral and the regression coefficients in the light intensity (i.e., the y-axis) and/or the wavelength (i.e. the x-axis) domain to quantify the difference between the test curve shape and the reference curve shape.

9. A method as in claim 8, wherein the reference curve comprises at least one of a calibration reference curve stored during calibration of the laser absorption spectrometer and a curve constructed using one or more stored calibration reference curves selected according to a composition of the background gas and/or the concentration of the target analyte.

10. A method as in claim 1, further comprising obtaining the test harmonic absorption curve, the obtaining comprising:
passing light from the light source through a volume of gas, the light comprising a scanned wavelength range and an imposed modulation frequency; and
converting a signal from the detector to the test harmonic curve, the converting comprising demodulating the signal at the first, the second or the higher order harmonic frequency of the imposed modulation frequency.

11. A method as in claim 1 wherein the volume of gas comprises one of a sample cell filled with a test gas comprising a known or unknown concentration of the target analyte, the sample cell filled with the background gas, a reference gas volume disposed in a path of the light and containing the test gas with the known or unknown concentration of the target analyte, and the reference gas volume disposed in the path of the light and containing only the background gas or gas mixture.

12. A method as in claim 11, wherein the sample cell comprises at least one of a multiple-pass configuration in which the light is reflected between one or more optically reflective mirrors while the light remains inside the sample cell; a multiple-pass configuration in which the light is refracted by one or more optical elements while the light remains inside the sample cell; a Herriot Cell; an off-axis optical resonator; a White cell; an optical cavity; a hollow core light guide; and a single pass configuration in which the light is not being reflected while the light remains inside the sample cell.

13. A method as in claim 1, further comprising checking fidelity of the laser absorption spectrometer by one or more of analyzing a premixed calibration sample from a premixed container, a prepared calibration sample generated using a permeation device, a non-absorbing zero gas, and a non-absorbing zero gas contained in a reference volume.

14. A method as in claim 1, wherein the laser absorption spectrometer further comprises a signal detection circuit that allows at least one of adjustment of a signal phase with respect to a modulation current phase of the laser light source, adjustment of frequency filters, and adjustment of DC and AC gain.

15. An apparatus comprising:
a non-transitory machine-readable storage medium storing instructions that, when executed by at least one processor, cause the at least one processor to perform operations comprising:
retrieving a reference harmonic absorption curve of a laser absorption spectrometer, the laser absorption spectrometer comprising a tunable or scannable laser light source and a detector, the reference harmonic absorption curve having a reference curve shape and comprising a first, second, or higher order harmonic signal of a reference signal generated by the detector in response to light passing from the laser light source through a reference gas or gas mixture, the reference gas or gas mixture comprising one or more of a target analyte and a background gas expected to be present during analysis of the target analyte; the reference harmonic absorption curve having been determined for the laser absorption spectrometer in a known or calibrated state;
comparing at least one portion of a test harmonic absorption curve having a test curve shape with at least one portion of the reference harmonic absorption curve to detect a difference between the test curve shape and the reference curve shape that exceeds a predefined allowed deviation and therefore indicates a change in an output of the laser light source relative to the known or calibrated state, wherein one or more portions of the test harmonic absorption curve is compared with one or more portions of the reference harmonic absorption curve arising due to absorption of the background gases and not by absorption of the target analyte; and
causing one or more operating and analytical parameters of the laser absorption spectrometer to be adjusted based on the comparing.

16. An apparatus as in claim 15, further comprising the at least one processor.

17. An apparatus as in claim 15, further comprising the laser absorption spectrometer.

18. An apparatus as in claim 17, wherein
the light source comprises at least one of a tunable diode laser, a tunable semiconductor laser, a quantum cascade laser, an intra-band cascade laser (ICL), a vertical cavity surface emitting laser (VCSEL), a horizontal cavity surface emitting laser (HCSEL), a distributed feedback laser, a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, a thermal emitter, and a device capable of generating frequency tunable light through nonlinear optical interactions; and
the detector comprises at least one of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, and a photo-multiplier.

19. An apparatus as in claim 17, wherein the volume of gas comprises one of a sample cell filled with a test gas comprising a known or unknown concentration of the target analyte, the sample cell filled with the background gas, a reference gas volume disposed in a path of the light and containing the test gas with the known or unknown concentration of the target analyte, and the reference gas volume disposed in the path of the light and containing only the background gas or gas mixture.

20. An apparatus as in claim 19, wherein the sample cell comprises at least one of a multiple-pass configuration in which the light is reflected between one or more optically reflective mirrors while the light remains inside the sample cell; a multiple-pass configuration in which the light is refracted by one or more optical elements while the light remains inside the sample cell; a Herriot Cell; an off-axis optical resonator; a White cell; an optical cavity; a hollow core light guide; and a single pass configuration in which the light is not being reflected while the light remains inside the sample cell.

21. An apparatus as in claim 17, wherein the laser absorption spectrometer further comprises a signal detection circuit that allows at least one of adjustment of a signal phase with respect to a modulation current phase of the laser light source, adjustment of frequency filters, and adjustment of DC and AC gain.

22. An apparatus as in claim 15, wherein the one or more operating and analytical parameters of the laser absorption spectrometer comprise at least one of laser light source parameters, detector parameters, and signal conversion parameters used in generating the test harmonic absorption curve from a signal produced by the detector.

23. An apparatus as in claim 22, wherein the laser light source parameters comprise at least one of a temperature, an operating current, a modulation current, a ramp current, and a phase of the laser light source; the detector parameters comprise at least one of a gain and a phase setting of a detector circuit; and the signal conversion parameters comprise at least one of a gain and a phase setting of a demodulating device.

24. An apparatus as in claim 15, wherein the output comprises a light intensity as a function of wavelength over a wavelength scan range.

25. An apparatus comprising:
  means for generating or receiving a reference harmonic absorption curve of a laser absorption spectrometer, the laser absorption spectrometer comprising a tunable or scannable laser light source and a detector, the reference harmonic absorption curve having a reference curve shape and comprising a first, second, or higher order harmonic signal of a reference signal generated by the detector in response to light passing from the laser light source through a reference gas or gas mixture, the reference gas or gas mixture comprising one or more of a target analyte and a background gas expected to be present during analysis of the target analyte, the reference harmonic absorption curve having been determined for the laser absorption spectrometer in a known or calibrated state;
  means for comparing at least one portion of a test harmonic absorption curve having a test curve shape with at least one portion of the reference harmonic absorption curve to detect a difference between the test curve shape and the reference curve shape that exceeds a predefined allowed deviation and therefore indicates a change in an output of the laser light source relative to the known or calibrated state, wherein one or more portions of the test harmonic absorption curve is compared with one or more portions of the reference harmonic absorption curve arising due to absorption of the background gases and not by absorption of the target analyte; and
  means for causing one or more operating and analytical parameters of the laser absorption spectrometer to be adjusted based on the comparing.

* * * * *